United States Patent [19]
Darcey

[11] Patent Number: 6,106,492
[45] Date of Patent: Aug. 22, 2000

[54] UNIVERSAL CARPAL TUNNEL WRIST SPLINT

[75] Inventor: Thomas D. Darcey, Mooresville, N.C.

[73] Assignee: Smith & Nephew, Inc., Charlotte, N.C.

[21] Appl. No.: 09/265,756

[22] Filed: Mar. 10, 1999

[51] Int. Cl.$^7$ .......................................................... A61F 5/00
[52] U.S. Cl. ........................ 602/8; 602/5; 602/6; 602/21
[58] Field of Search ................................... 602/5, 7, 8, 9, 602/6; 428/246, 251, 285, 68, 76, 36, 74; 220/438; 206/440, 441, 411, 412, 413, 447, 484

[56] References Cited

U.S. PATENT DOCUMENTS

| | | |
|---|---|---|
| 4,770,299 | 9/1988 | Parker ...................................... 206/409 |
| 5,755,678 | 5/1998 | Parker et al. ................................ 602/6 |
| B1 4,411,262 | 7/1985 | von Bonin et al. ......................... 602/8 |

Primary Examiner—Kim M. Lee
Attorney, Agent, or Firm—Adams, Schwartz & Evans, P.A.

[57] ABSTRACT

A carpal tunnel splint for being custom-fitted to a hand and wrist to be supported, and comprising an elongate, narrow flexible inner cushion layer for being placed on and conformed to the shape of the hand and wrist, an initially flexible intermediate layer overlying the inner cushion layer and an intermediate layer comprised of a fabric impregnated with a moisture-curable resin which hardens upon curing to form a rigid structure of the fabric which retains a shape into which it is molded during curing, thereby also holding the flexible inner cushion layer in a conforming shape against the hand and wrist. A flexible protective outer layer overlies the intermediate layer and is attached to the inner cushion layer for enclosing the intermediate layer and forming the inner layer, intermediate layer and outer layer into a single, integrated elongated, narrow splint structure.

14 Claims, 7 Drawing Sheets

UNIVERSAL CARPAL TUNNEL WRIST SPLINT

TECHNICAL FIELD AND BACKGROUND OF THE INVENTION

This invention relates to a custom-fitted carpal tunnel syndrome. The disclosure of this application includes a package in which a pair of splints are contained for ease of sale, distribution and use. This is a convenient manner in which to distribute the product, since the splints as made may be used in pairs—one each for the volar and dorsal aspects of the hand. However, the splint according to the invention can be packaged and dispensed in single, moisture-proof-packages or in any other suitable manner.

Carpal tunnel syndrome results from compression of the median nerve that travels through the wrist supplying the thumb aspect of the hand. This compression produces numbness, tingling, and pain in the first three fingers and the thumb side of the hand. Occasionally, it also produces pain and paresthesia in the arm and shoulder. The pain may be more severe while sleeping because of the way the hand is positioned. With time, the muscles in the hand on the thumb side can weaken and atrophy.

Causes of carpal tunnel syndrome are controversial, but have been attributed to types of effort which require repeated forceful movements with the wrist extended, such as using a screwdriver or a computer keyboard. Pregnant women and individuals who have diabetes or an underactive thyroid gland are at increased risk of developing carpal tunnel syndrome.

Treatment of severe cases include corticosteroid injections into the affected nerve, or surgery to relieve pressure on the nerve. This is most often done by releasing the bands of fibrous tissue that place pressure on the median nerve.

Prompt treatment upon onset can minimize pain and disability and reduce the extent of treatment needed. One form of early treatment is to splint the hand and wrist to provide support to the muscles of the hand and wrist. This treatment, combined with rest and correction of the suspected cause (for example, repositioning or changing a computer keyboard), can often avoid the need for injections and surgery.

Prior art splints often include a soft component to place near the skin and a hard, shell-like outer cover. The soft component is intended not only to provide a cushion, but also to accommodate itself to the varying configurations of differing sized and shaped hands.

Other splints are glove-like in design and are provided with bendable plastic or metal stays which are bent to position the hand and wrist in the desired position.

Some other prior art splints are constructed of or include thermosetting materials, which are heated and then formed to the hand and wrist while heated. These products require a source of heat, and are susceptible to either over-or-underheating. In addition, body heat itself can soften or at least increase the flexibility of the splint, thereby decreasing the effectiveness of the protection offered by the splint. Insofar as is known, no previous treatment for carpal tunnel syndrome splints both the volar and dorsal aspects of the wrist on both the hand and lower arm sides of the wrist. Generally, prior art splints are positioned only on the dorsal aspect of the wrist.

The present invention permits quick and easy application of a protective splint to the hand in such a way as to achieve a true custom fit from a single, universal design. The moisture curable resin system used results in a very rigid splint which holds the shape into which it is molded. No heat is required, and a source of water is the only additional material necessary to harden the splint. Atmospheric moisture alone will cure the splint into its hardened position in a relatively short period of time, but the resin in or on the splint will typically be activated by dipping in water. The splint is inexpensive, easy to fabricate, easy to fit and comfortable to wear. Since the splint is a single shape and size, hospitals, clinics and other emergency care facilities can easily and inexpensively maintain a necessary inventory of splints.

Application of two splints to the injury—one on the volar aspect and one on the dorsal aspect—achieves a true four-point fixation of the injury. This provides greater support while reducing the extent of residual movement of the splinted hand and wrist.

SUMMARY OF THE INVENTION

Therefore, it is an object of the invention to provide a carpal tunnel splint which is a universal size and shape.

It is another object of the invention to provide a carpal tunnel splint which is easy to fabricate.

It is an object of the invention to provide a carpal tunnel splint which can be easily placed on and removed from the hand and wrist by the patient.

It is another object of the invention to provide a carpal tunnel splint wherein two or more such splints are packaged in a single moisture-impervious package for ease of removal and use.

It is another object of the invention to provide a carpal tunnel splint wherein two identical splints are interchangeable from the volar to dorsal aspect of the hand and between left hand and right hands.

It is another object of the invention to provide a carpal tunnel splint wherein one splint is placed on the volar aspect and one splint is placed on the dorsal aspect of a hand and wrist to achieve four-point fixation of the injury.

It is another object of the invention to provide a carpal tunnel splints which hardens in the presence of moisture to form a very rigid but very lightweight protective splint.

It is another object of the invention to provide a carpal tunnel splint which is stored in a moisture-proof pouch until ready for application to the body part to be protected, and which is also stored in a secondary, cure-retarding inner package within the moisture-proof pouch.

These and other objects of the present invention are achieved in the preferred embodiments disclosed below by providing a carpal tunnel splint for being custom-fitted to a hand and wrist to be supported, and comprising an elongate, narrow flexible inner cushion layer for being placed on and conformed to the shape of the hand and wrist, an initially flexible intermediate layer overlying the inner cushion layer and an intermediate layer comprised of a fabric impregnated with a moisture-curable resin which hardens upon curing to form a rigid structure of the fabric which retains a shape into which it is molded during curing, thereby also holding the flexible inner cushion layer in a conforming shape against the hand and wrist. A flexible protective outer layer overlies the intermediate layer and is attached to the inner cushion layer for enclosing the intermediate layer and forming the inner layer, intermediate layer and outer layer into a single, integrated elongated, narrow splint structure.

According to one preferred embodiment of the invention, the fabric comprises a plurality of overlaid thicknesses of fiberglass.

According to another preferred embodiment of the invention, the plurality of thicknesses of fiberglass comprises at least five thicknesses and no more than seven thicknesses.

According to yet another preferred embodiment of the invention, the outer layer comprises a fabric having a strap-retaining loop positioned thereon and extending along a major lengthwise dimension thereof for receiving a splint-retaining strap therein.

According to yet another preferred embodiment of the invention, the outer layer comprises a fabric having a first strap-retaining loop positioned on one end thereof and extending along a major lengthwise dimension thereof, and a second strap-retaining loop positioned on an opposite end thereof and extending along the major lengthwise dimension thereof.

According to yet another preferred embodiment of the invention, the first strap-retaining loop has a predetermined relatively wide width for receiving a relatively wide splint-retaining strap, and the second strap-retaining loop has a predetermined relatively narrow width for receiving a relatively narrow splint-retaining strap.

Preferably, the outer layer comprises a fabric having a first strap-retaining loop positioned on one end thereof and extending along a major lengthwise dimension thereof for receiving a splint-retaining strap therethrough, and second and third laterally-spaced apart, strap-retaining loops positioned on an opposite end thereof and extending along the major lengthwise dimension thereof for receiving a splint-retaining strap therethrough.

According to yet another preferred embodiment of the invention, the first strap-retaining loop is relatively wide for receiving a relatively wide strap, and the second and third retaining loops are relatively narrow for receiving a relatively narrow strap.

According to yet another preferred embodiment of the invention, the relatively narrow loops are positioned on an end of the splint adapted to be formed to the hand and the relatively wide loop is positioned on an end of the splint adapted to be formed to the wrist and lower forearm of the wearer.

A carpal tunnel splint assembly according to the invention comprises a splint and an elongate strap for securing the splint to the hand and wrist.

According to yet another preferred embodiment of the invention, a carpal tunnel splint assembly is provided, and includes a first splint for being positioned against and formed to the volar aspect of the hand and wrist, a second splint for being positioned against and formed to the dorsal aspect of the hand and wrist, and first and second elongate straps for retaining the first and second splints against the volar and dorsal aspects of the hand and wrist.

According to yet another preferred embodiment of the invention, the carpal tunnel splint assembly includes a moisture-proof pouch in which the splint is contained in a flexible condition in moisture-free conditions until being opened immediately prior to application to the hand and wrist.

According to yet another preferred embodiment of the invention, the outer moisture-proof protective pouch is formed of a laminated structure having at least one layer of plastic film and at least one layer of aluminum foil bonded to the plastic film.

According to yet another preferred embodiment of the invention, a carpal tunnel splint assembly for being custom-fitted to a hand and wrist to be supported comprises first and second elongate, narrow splints, each of the first and second splints having an initially flexible layer comprised of a fabric impregnated with a moisture-curable resin which hardens upon curing to form a rigid structure of the fabric which retains a body part-defined shape into which it is molded during curing. First and second inner storage pouches are provided, and are constructed of a plastic film having moisture-transmission retarding properties. One of the first or second splints is sealed in respective ones of the first and second storage pouches. A single, outer moisture-proof protective pouch is provided within which the splint-containing storage pouches are sealed in the absence of moisture until the splint is to be molded to the body part to be protected. The outer moisture-proof protective pouch is formed of a laminated structure having at least one layer of plastic film and at least one layer of aluminum foil bonded to the plastic film.

According to yet another preferred embodiment of the invention, the plastic film has a thickness of between 1.5 mils and 4 mils, and at least one plastic film layer has a thickness of 2 mils and the aluminum foil layer has a thickness of 0.5 mils.

According to yet another preferred embodiment of the invention, the outer moisture-proof protective pouch includes a laminated layer of nylon film.

BRIEF DESCRIPTION OF THE DRAWINGS

Some of the objects of the invention have been set forth above. Other objects and advantages of the invention will appear as the invention proceeds when taken in conjunction with the following drawings, in which.

DESCRIPTION OF THE PREFERRED EMBODIMENT AND BEST MODE

Figure 1:
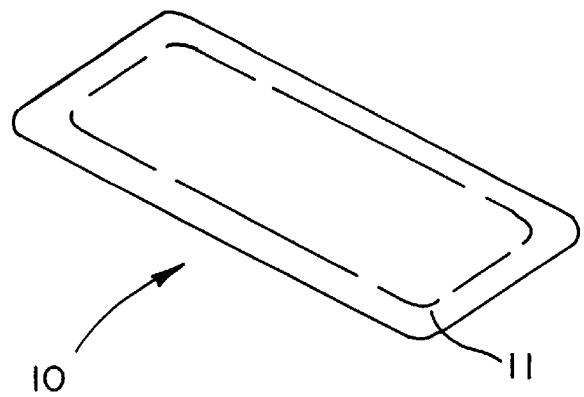
FIG. 1 is a perspective view of a splint assembly according to a preferred embodiment of the invention comprising a single splint in a single moisture-proof pouch.

Referring now specifically to the drawings, FIG. 1 illustrates a splint assembly 10 according to an embodiment of the invention. The splint assembly 10 includes as its outermost protective enclosure an outer moisture-impervious foil and laminated pouch 11 in which the splint according to the disclosure of this application is sealed in the absence of moisture. The preferred structure of the outer moisture-impervious pouch 11 includes a 0.5 mil aluminum foil sheet sandwiched between two layers of low density polyethylene film, each layer having a thickness of 2 mils. Additionally, the pouch 11 can include an outer layer of laminated 60 gauge bi-axially oriented nylon film. This laminate structure, when properly sealed, will prevent moisture intrusion indefinitely.

Figure 2:
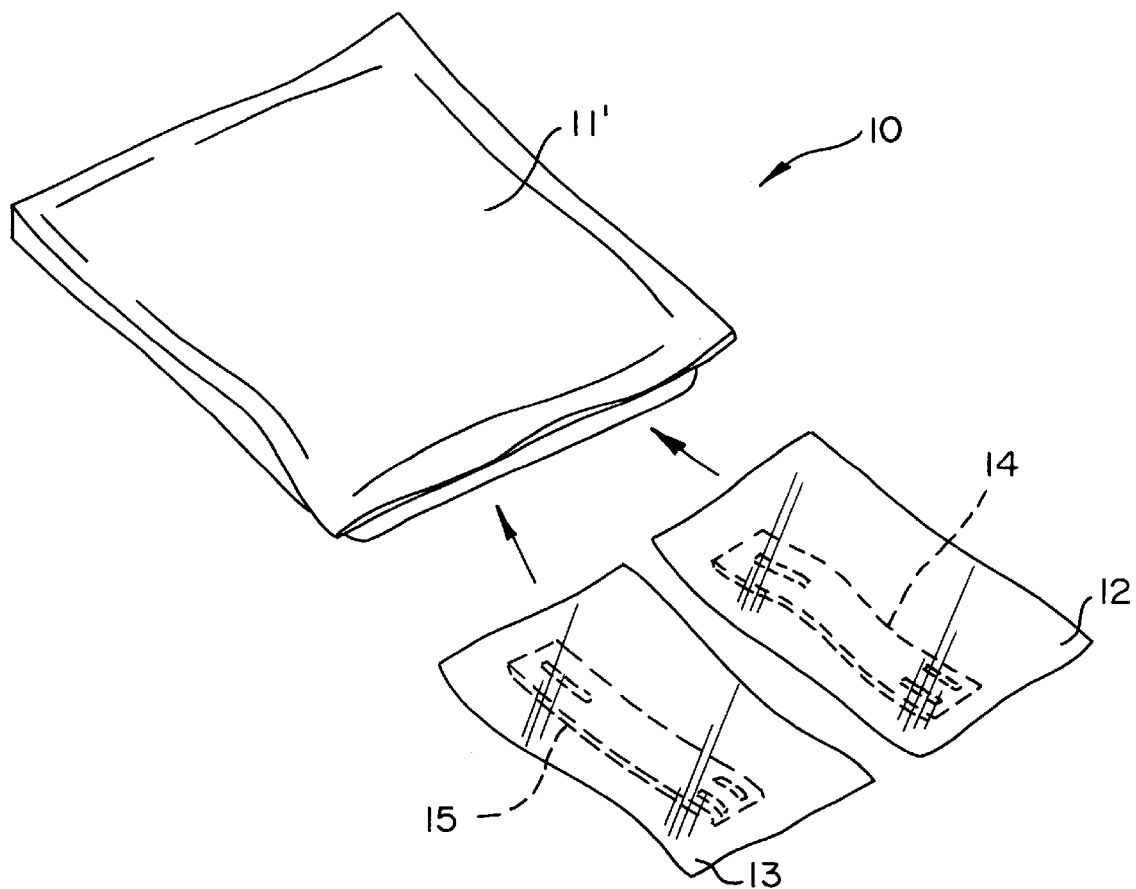
FIG. 2 is an exploded perspective view showing an outer, moisture proof packaging within which the splints are stored, and the inner, moisture-retardant pouches in which the splints are also contained in accordance with an alternative embodiment of the invention.

Referring now to FIG. 2, in an alternative embodiment of the splint assembly 10', the outer pouch 11' contains two inner, moisture-retardant plastic film pouches 12 and 13, in which are sealed respective splints 14 and 15. The preferred embodiment of the plastic film from which the pouches 12 and 13 are constructed is a 1.5 mil low density polyethylene, with thicknesses up to 4 mils suitable, as well. The pouches 12 and 13 are sufficiently thin and porous that moisture will penetrate, but the penetration is sufficiently retarded in comparison with exposure directly to atmospheric humidity that curing occurs at a greatly reduced rate.

The splints 14 and 15 are sealed in the inner pouches 12 and 13 in the absence of moisture immediately prior to being sealed into the outer, moisture impervious pouch 11'. Assembled in this manner, the splint assembly 10' permits the splints 14 and 15 to be sold in pairs and in such a manner that they have an indefinite shelf life.

Figure 3:
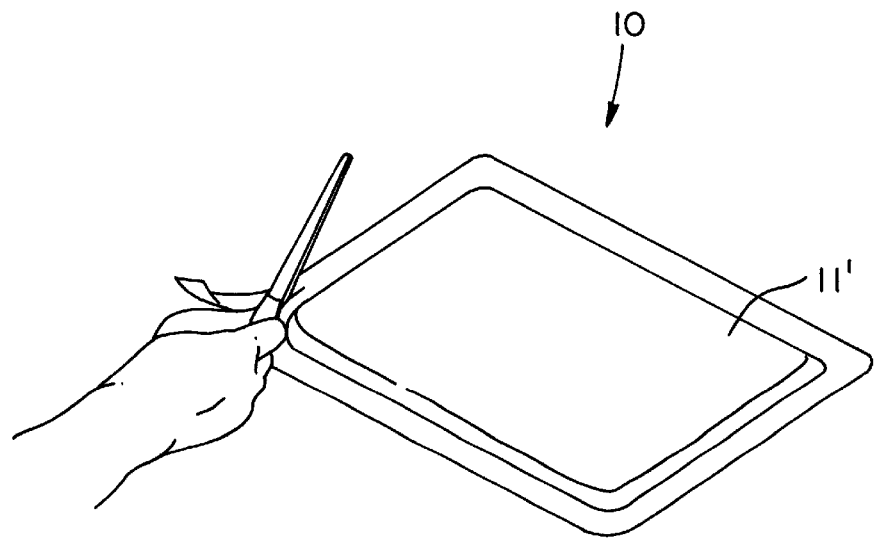
FIG. 3 is a perspective view showing the opening of the outer, moisture-proof-pouch.

The moisture-impervious foil and plastic laminated pouch 11 is opened with scissors or a knife, as shown in FIG. 3, and the inner moisture retardant pouches 12 and 13 are removed. Pouch 12 is opened, while pouch 13 is left sealed. This greatly retards penetration of moisture into the splint 14 while splint 15 is formed to the hand and wrist.

Figure 4:
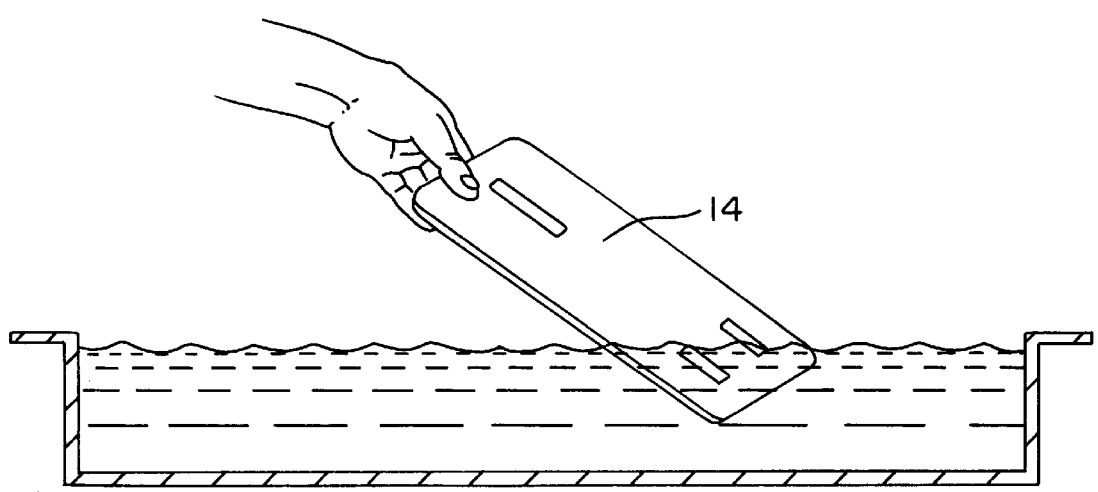
FIG. 4 illustrates that the splint is wetted in water before application.

As is shown in FIG. 4, the splint 14 is dipped in water to activate the moisture-curable resin with which the splint 14 is impregnated or coated. The wet splint 14 is then applied to the either the volar or dorsal aspect of the hand and wrist to be supported. The splint 14 will harden within a matter of minutes, and will retain the conformation in which it was held during curing.

The pouch 13 can be opened immediately after application of the splint 14, or can be opened up to several hours later without significant hardening of the splint 15. When pouch 13 is opened, the splint 15 is removed and applied as described above with reference to splint 14. Since both splints 14 and 15 are identical in structure and are applied in the same manner, further description of the invention refers only to splint 14.

Figure 5:
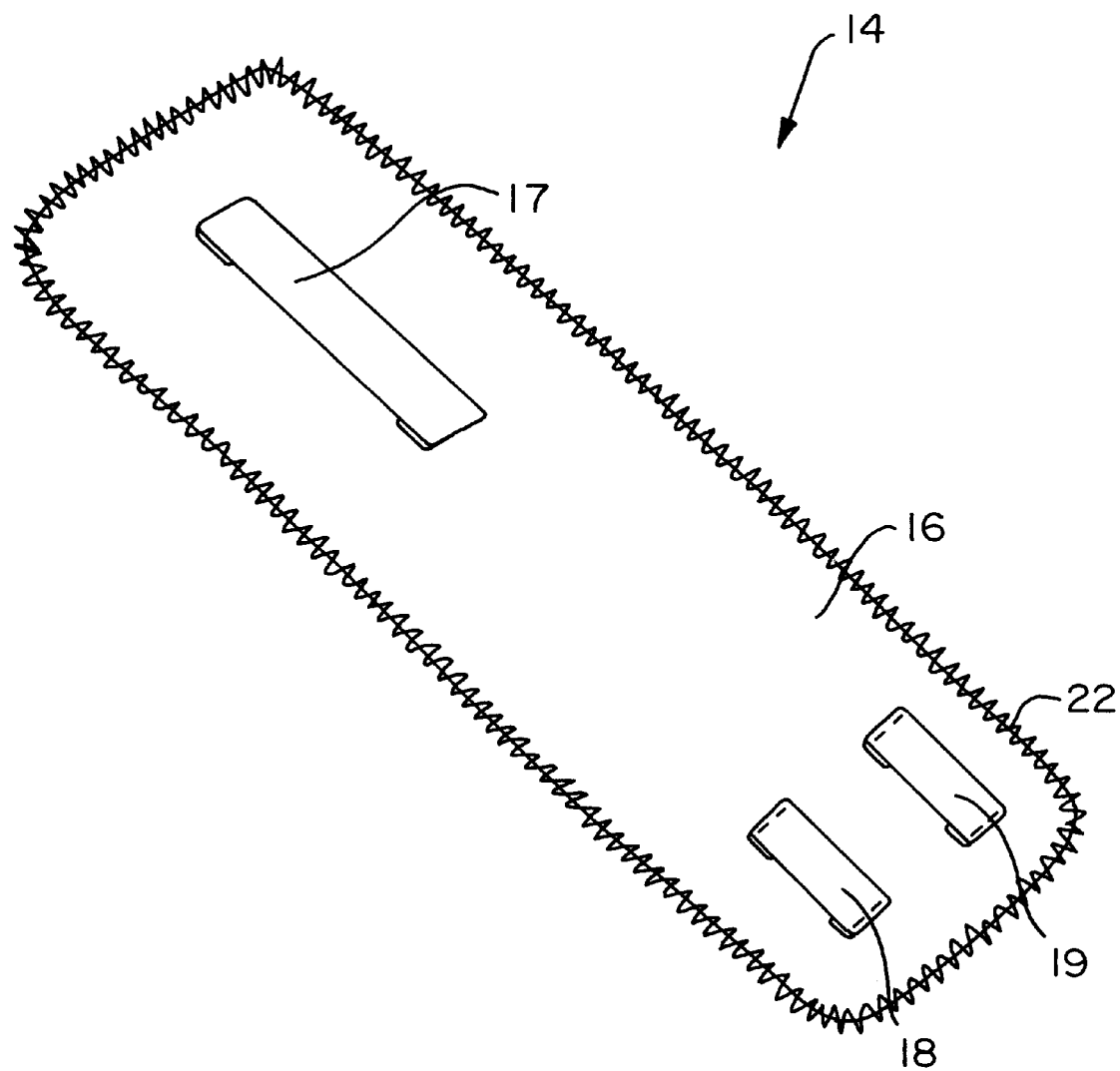
FIG. 5 is a perspective view of the outer side of the splint.
Figure 7:
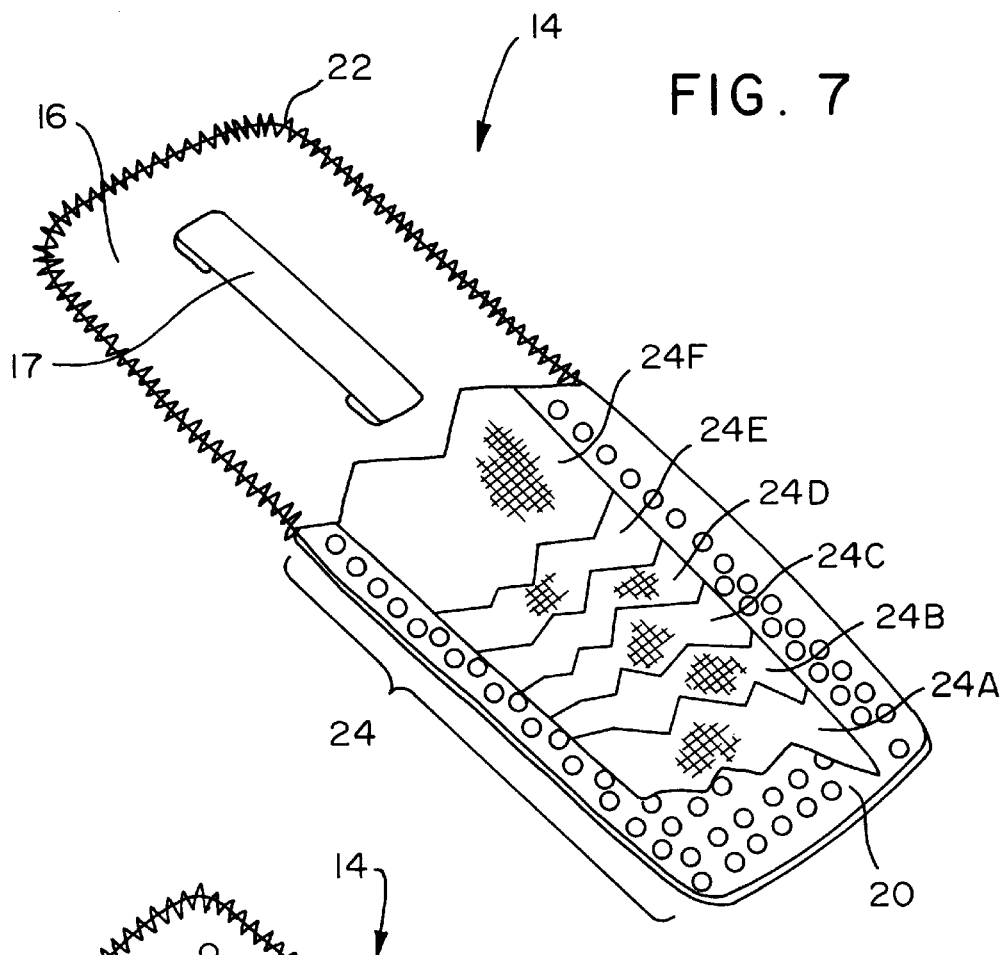
FIG. 7 is a perspective view of a splint according to an embodiment of the invention, with parts broken away and with the fiberglass intermediate layer exposed for clarity.
Figure 6:
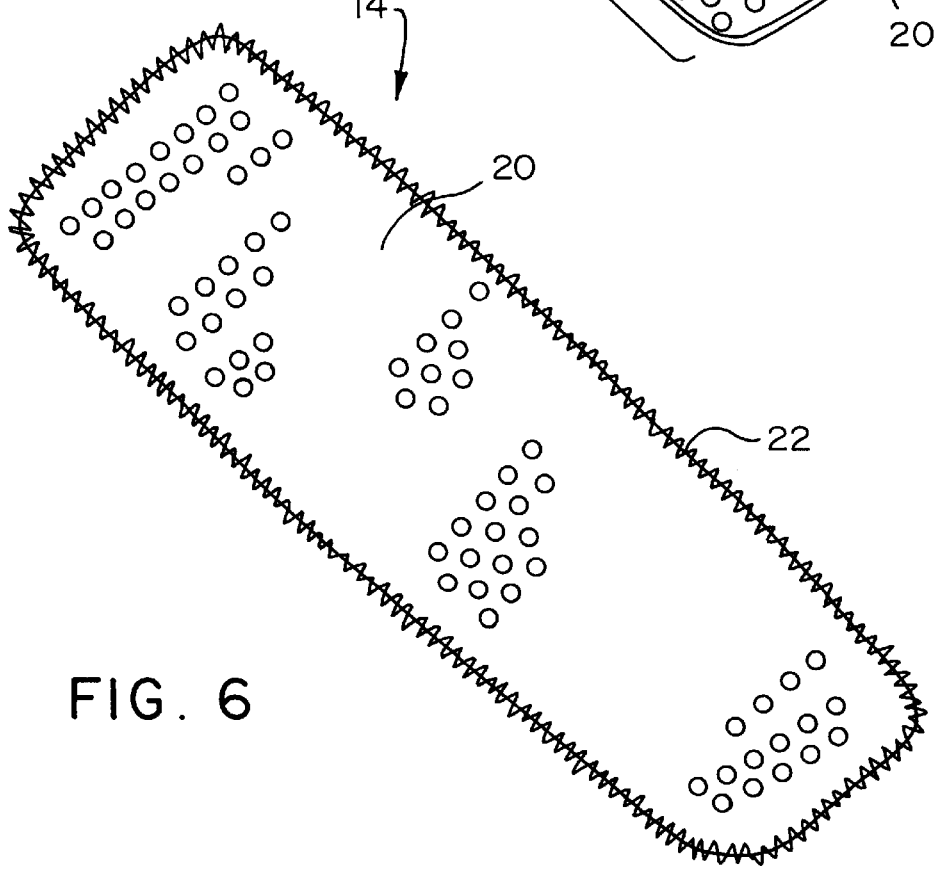
FIG. 6 is a perspective view of the inner side of the splint.

Referring now to FIGS. 5, 6 and 7, the splint 14 is illustrated and described more specifically. As is shown in FIG. 5, the outer layer of the splint 14 comprises a fabric casing 16. A relatively wide strap loop 17 is sewn to the fabric adjacent one end of the splint 14, and a pair of relatively narrow strap loops 18 and 19 are sewn to the fabric adjacent the other end of the splint 14.

As is shown in FIG. 6, a flexible inner cushion layer 20 is provided for being placed closest to the body member. Inner cushion layer 20 is preferably a laminated one-eighth inch, four pound EVA (ethylene vinyl acetate) micro-perf closed cell foam. The cushioning provides a comfortable surface next to the skin. The EVA is flexible enough to bend easily with the other components of the splint 14. The fabric outer layer 16 and the inner cushion layer 20 are joined around the perimeter by overedge sewing stitches 22.

Referring now to FIG. 7, an initially flexible intermediate layer 24 is sandwiched between the outer layer 16 and the inner layer 20. The intermediate layer 24 is preferably formed of fiberglass fabric layers 24A-F impregnated with a moisture-curable resin which hardens upon curing to form a rigid structure which retains shape of the hand and wrist onto which it is molded prior to curing. The particular embodiment illustrated in this application contains six layers of fiberglass fabric, but many other variations are equally suitable.

The fiberglass fabric layers 24A-F are impregnated or coated with a moisture-curable resin such as polyisocyanate as described in full in the present applicant's U.S. Pat. No. 4,770,299. This reactive system remains stable when maintained in substantially moisture-free conditions, such as in the moisture-impervious pouch 11, but hardens upon exposure to sufficient moisture to form a rigid, self-supporting structure. A typical formulation of the reaction system is set forth in the following table:

| Typical Formulation: | | |
|---|---|---|
| Isonate↓ 143L | or | |
| Mondur↓ CD | or polyisocyanate | 50.0% |
| Rubinate↓ XI168 | | |
| Pluracol↓ P1010 | polyol | 46.6% |
| DC-200 Silicone | defoaming agent | 0.30% |
| Benzoyl Chloride | stabilizer | 0.10% |
| Thancat↓ DM-70 | catalyst | 3.0% |
| | | 100% |

A complete discussion of the parameters of the reactive system, the manner of production and the variables which apply are found in U.S. Pat. No. 4,411,262.

The polyisocyanate resin remains in a viscous, liquid unhardened state so long as the resin is not exposed to moisture. This permits the fiberglass intermediate layer 24 and any flexible structure, such as the inner cushion layer 20, to remain flexible and moldable so long as the resin is not exposed to moisture, and for a relatively short period of time after exposure to moisture.

The curing time can be controlled to some extent by the quantity of water to which the resin is exposed. For example, exposure to water by dipping will result in quite rapid curing, while merely allowing the resin to be exposed to air will cause long curing times proportional to the amount of humidity in the air to which it is exposed.

In accordance with the invention, the individual fiberglass fabric layers 24A-F are preferably die-cut to shape. The various fabric layers 24A-F preferably have the same width, but may have alternatively vary, and the degree of overlap and non-overlap resulting from the differing widths has the effect of providing variable thickness with a relatively thick predetermined area where increased rigidity is desirable and a relatively thin area where increased flexibility is desirable. The manner of varying the widths of the fabric layers 15A-F is described in detail in Applicant's prior U.S. Pat. No. 5,755,678.

Alternatively, some of the layers 24A-F may be of other material, such as polypropylene, which offers additional flexibility and some cost savings in material.

Splints 14 may be applied to either of the volar or dorsal aspects of the hand and wrist, or may be applied to both aspects, depending on the severity of the injury and the degree of support desired. Preferably, two splints 14 are applied in the manner described and illustrated. This achieves a true four-point fixation of the injury and enhances both the support offered to the injury and reduces residual movement, thus speeding healing.

Figure 8:
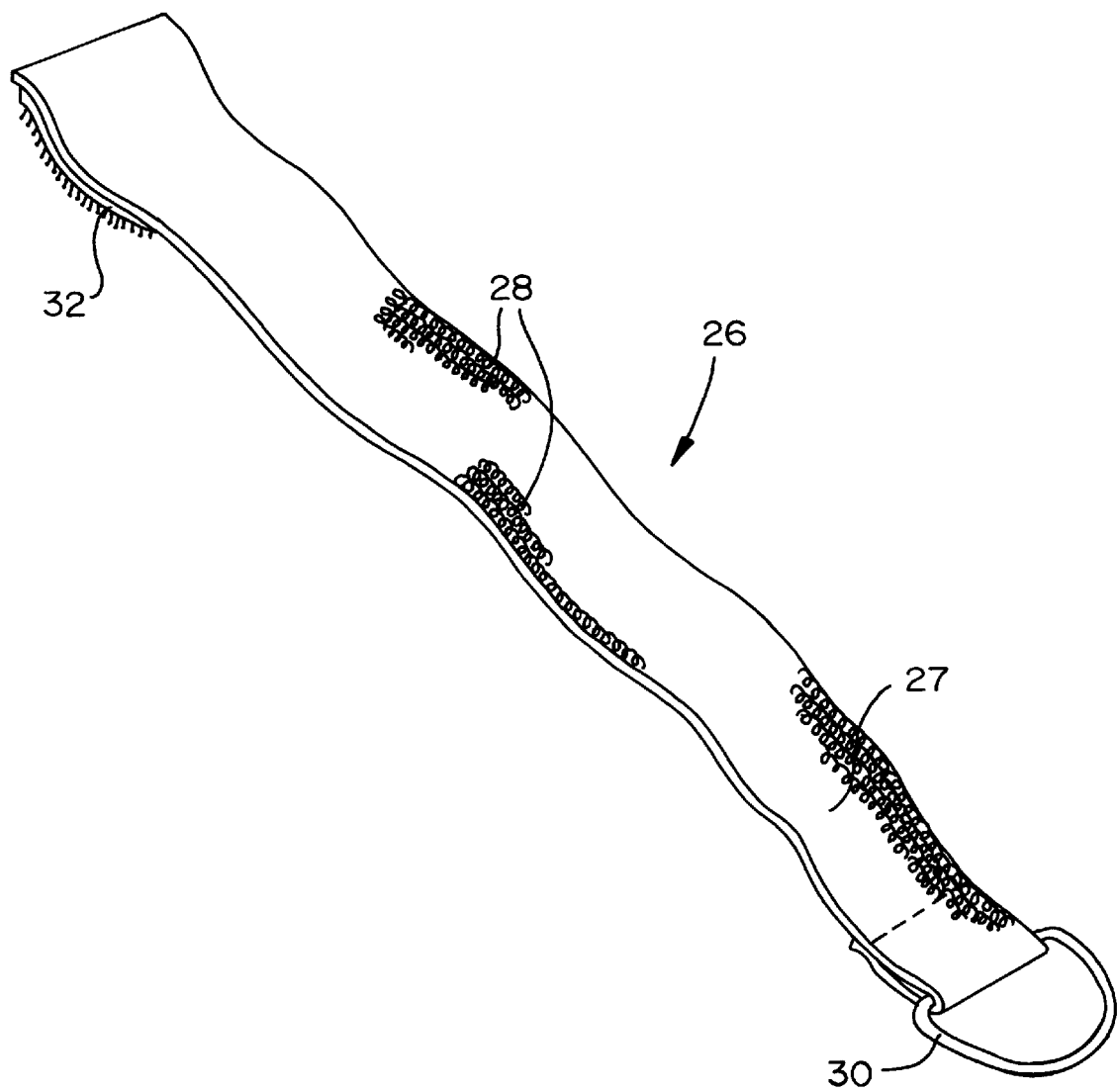
FIG. 8 is a perspective view of a strap of the type used to secure the splint or splints to the hand and wrist.

The splints are applied to the hand and wrist with straps 26, such as shown in FIG. 8. Such straps are typically formed of a narrow length of woven or knitted material 27 having a loose, fibrous covering 28 on the surface. A D-ring 30 is secured to one end of the strap, and a patch of hook material 32 is sewn or glued to the other end. The strap 26 is formed into a loop by passing the strap through the D-ring 30 and securing the end of the strap 26 to the fibrous covering 28 at the desired position. As described below, the width of the straps 26 varies depending on where they are positioned on the splint 14.

Figure 9:
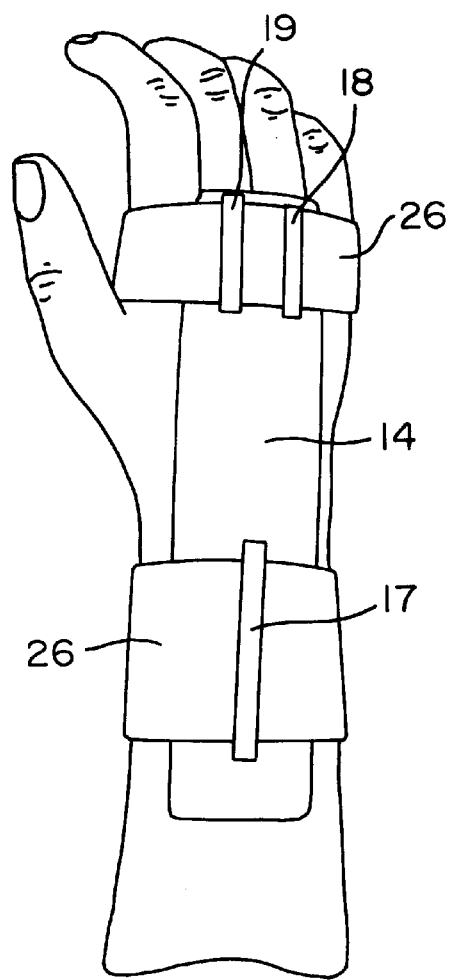
FIG. 9 is a view of a splint secured to the dorsal aspect of the hand and wrist.
Figure 10:
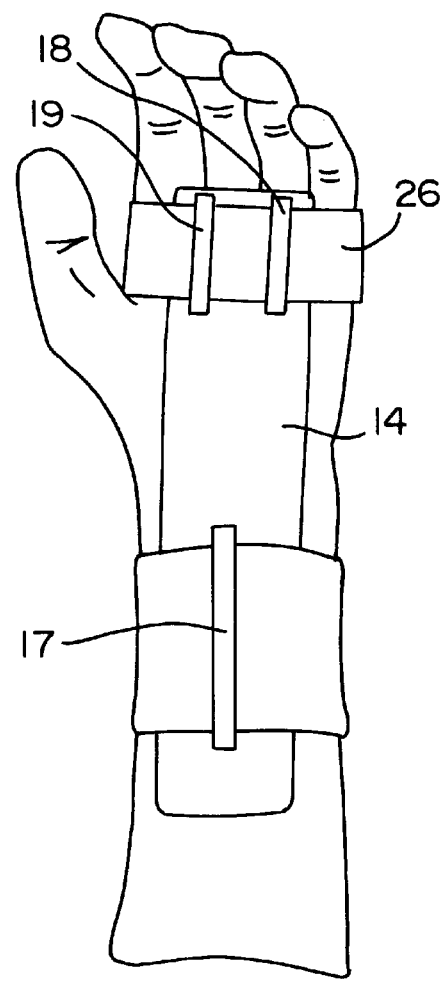
FIG. 10 is a view of a splint secured to the volar aspect of the hand and wrist.

Referring now to FIGS. 9 and 10, splints 14 are applied to the hand and wrist by wetting them as described above, The splint 14 is wetted. A narrow strap 26 is passed through the two narrow loops 18, 19 and a wide strap 26 through the wide loop 17. If two splints 14 are to be used, a second splint 14 is also applied to the narrow and wide straps 26. The straps 26 are then placed onto the hand and wrist and the two splints 14 are positioned so that one is longitudinally aligned with the volar aspect of the hand and wrist and the other is longitudinally aligned with the dorsal aspect of the hand and wrist. The straps are then loosened or tightened if necessary to the correct tightness.

Figure 11:
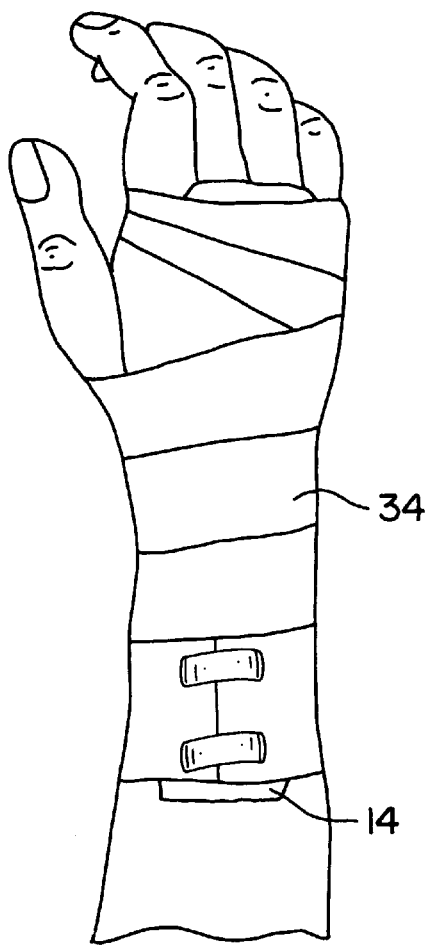
FIG. 11 is a view of a splint secured to the dorsal aspect of the hand and wrist and overwrapped with an elastic bandage.
Figure 12:
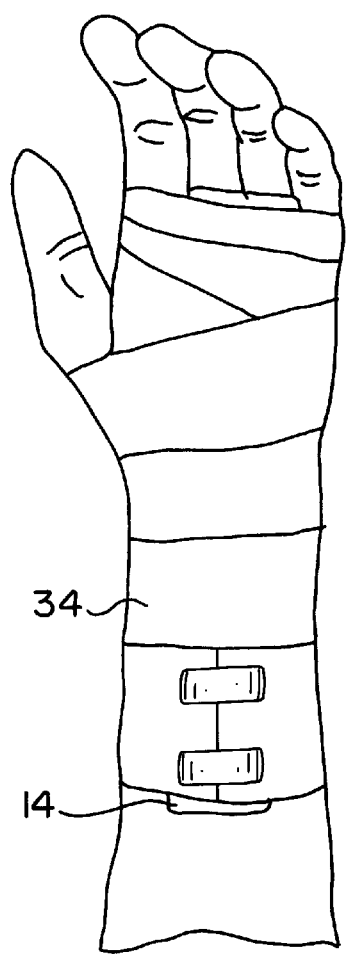
FIG. 12 is a view of a splint secured to the volar aspect of the hand and wrist and overwrapped with an elastic bandage.

The hand and wrist is then overwrapped with an elastic bandage 34, as shown in FIGS. 11 and 12. The elastic bandage 34 remains on the hand and wrist at least for a sufficient period of time for the splints 14 to completely harden into the proper conformation on the hand and wrist. The elastic bandage 34 may be used continuously or intermittently, or the splints 14 may be worn after hardening without the elastic bandage 34. The patient must be cautioned not to attempt to flex or articulate the hand or wrist during the period of splint hardening.

One preferred embodiment of the splint 14 has the following specifications:

| | |
|---|---|
| Overall length | 7.5 inches |
| Overall width | 2.5 inches |
| Narrow strap loop | .75 inches seam-to-seam |
| Width of narrow strap | .625 inches |
| Length of narrow strap | 14 inches |
| Wide strap loop | 2.125 inches seam-to-seam |
| Width of wide strap | 2 inches |
| Length of wide strap | 14 inches |
| Outer layer | Polyester sheeting |
| Inner layer | .125 inch microperf EVA closed cell foam |
| Width of fiberglass intermediate layers | 1 inch |
| Length of fiberglass intermediate layers | 6.75 inches |
| Number of fiberglass layers | 6 |
| Wrap | 2 inch × 5 yard stretch elastic-free elastic bandage |

A universal carpal tunnel splint is described above. Various details of the invention may be changed without departing from its scope. Furthermore, the foregoing description of the preferred embodiment of the invention and the best mode for practicing the invention are provided for the purpose of illustration only and not for the purpose of limitation—the invention being defined by the claims.

I claim:

1. A carpal tunnel splint for being custom-fitted to a hand and wrist to be supported, and comprising:
   (a) first splint for being positioned against and formed to the volar aspect of the hand and wrist, and a second splint for being positioned against and formed to the dorsal aspect of the hand and wrist, each of said first and second splints comprising:
      (i) an elongate, narrow flexible inner cushion layer for being placed on and conformed to the shape of the hand and wrist;
      (ii) an initially flexible intermediate layer overlying the inner cushion layer, said intermediate layer comprised of a fabric impregnated with a moisture-curable resin which hardens upon curing to form a rigid structure of the fabric which retains a shape into which it is molded during curing, thereby also holding the flexible inner cushion layer in a conforming shape against the hand and wrist;
      (iii) a flexible protective outer layer overlying the intermediate layer and attached to the inner cushion layer for enclosing the intermediate layer and forming the inner layer, intermediate layer and outer layer into a single, integrated elongated, narrow splint structure; and
   (b) a strap for retaining said first and second splints in position on the hand and wrist during use of said splint assembly.

2. The carpal tunnel splint according to claim 1, wherein said fabric comprises a plurality of overlaid thicknesses of fiberglass.

3. The carpal tunnel splint according to claim 2, wherein said plurality of thicknesses of fiberglass comprises at least five thicknesses and no more than seven thicknesses.

4. The carpal tunnel splint according to claim 2, wherein said outer layer comprises a strap-retaining loop positioned thereon and extending along a major lengthwise dimension thereof for receiving a splint-retaining strap therein.

5. The carpal tunnel splint according to claim 2, wherein said outer layer comprises a first strap-retaining loop positioned on one end thereof and extending along a major lengthwise dimension thereof, and a second strap-retaining loop positioned on an opposite end thereof and extending along the major lengthwise dimension thereof.

6. The carpal tunnel splint according to claim 5, wherein said first strap-retaining loop has a predetermined relatively wide width for receiving a relatively wide splint-retaining strap, and said second strap-retaining loop has a predetermined relatively narrow width for receiving a relatively narrow splint-retaining strap.

7. The carpal tunnel splint according to claim 6, wherein said first strap-retaining loop is relatively wide for receiving a relatively wide strap, and said second and third retaining loops are relatively narrow for receiving a relatively narrow strap.

8. The carpal tunnel splint according to claim 7, wherein said relatively narrow loops are positioned on an end of the splint adapted to be formed to the hand and the relatively wide loop is positioned on an end of the splint adapted to be formed to the wrist and lower forearm of the wearer.

9. The carpal tunnel splint according to claim 2, wherein said outer layer comprises a first strap-retaining loop positioned on one end thereof and extending along a major lengthwise dimension thereof for receiving a splint-retaining strap therethrough, and second and third laterally-spaced apart, strap-retaining loops positioned on an opposite end thereof and extending along the major lengthwise dimension thereof for receiving a splint-retaining strap therethrough.

10. A carpal tunnel splint assembly according to claim 1, 4, 5, 6, 7, 8, and 9, and including a moisture-proof pouch in which the splint is contained in a flexible condition in moisture-free conditions until being opened immediately prior to application to the hand and wrist.

11. The carpal tunnel splint assembly according to claim 10, wherein said outer moisture-proof protective pouch is formed of a laminated structure having at least one layer of plastic film and at least one layer of aluminum foil bonded to the plastic film.

12. A carpal tunnel splint assembly for being custom-fitted to a hand and wrist to be supported, and comprising:

(a) first and second elongate, narrow splints, each of said first and second splints having an initially flexible layer comprised of a fabric impregnated with a moisture-curable resin which hardens upon curing to form a rigid structure of the fabric which retains a body part-defined shape into which it is molded during curing;

(b) first and second inner storage pouches constructed of a plastic film having moisture-transmission retarding properties, one of said first or second splints being sealed in respective ones of the first and second storage pouches; and (c) a single, outer moisture-proof protective pouch within which elements (a) and (b) are sealed in the absence of moisture until the splint is to be molded to the body part to be protected, said outer moisture-proof protective pouch formed of a laminated structure having at least one layer of plastic film and at least one layer of aluminum foil bonded to the plastic film.

13. The carpal tunnel splint assembly according to claim 12, wherein said plastic film has a thickness of between 1.5 mils and 4 mils, and wherein the at least one plastic film layer has a thickness of 2 mils and said aluminum foil layer has a thickness of 0.5 mils.

14. The carpal tunnel splint assembly according to claim 12, wherein said outer moisture-proof protective pouch includes a laminated layer of nylon film.

* * * * *